US010557744B2

(12) United States Patent
Kuhnen et al.

(10) Patent No.: US 10,557,744 B2
(45) Date of Patent: Feb. 11, 2020

(54) APPARATUS FOR DETERMINING AND/OR MONITORING AT LEAST ONE PROCESS VARIABLE

(71) Applicant: Endress+Hauser SE+Co. KG, Maulburg (DE)

(72) Inventors: Raphael Kuhnen, Schliengen (DE); Ira Henkel, Wehr (DE); Dietmar Frühauf, Lörrach (DE)

(73) Assignee: Endress+Hauser SE+Co. KG, Maulburg (DE)

( * ) Notice: Subject to any disclaimer, the term of this patent is extended or adjusted under 35 U.S.C. 154(b) by 0 days.

(21) Appl. No.: 16/315,373

(22) PCT Filed: Jun. 26, 2017

(86) PCT No.: PCT/EP2017/065631
§ 371 (c)(1),
(2) Date: Jan. 4, 2019

(87) PCT Pub. No.: WO2018/007178
PCT Pub. Date: Jan. 11, 2018

(65) Prior Publication Data
US 2019/0257683 A1    Aug. 22, 2019

(30) Foreign Application Priority Data
Jul. 5, 2016 (DE) .................. 10 2016 112 309

(51) Int. Cl.
G01F 23/296    (2006.01)
G01N 9/00    (2006.01)
(Continued)

(52) U.S. Cl.
CPC ...... *G01F 23/2966* (2013.01); *G01F 23/2968* (2013.01); *G01N 9/002* (2013.01);
(Continued)

(58) Field of Classification Search
None
See application file for complete search history.

(56) References Cited

U.S. PATENT DOCUMENTS 2,910,999 A * 11/1959 Kimberly ................. G05D 9/12
137/386
3,625,058 A * 12/1971 Dress et al. ......... G01F 23/2967
73/290 V
(Continued)

FOREIGN PATENT DOCUMENTS

DE    1773815 A1    2/1972
DE    3601704 A1    7/1987
(Continued)

OTHER PUBLICATIONS

Search Report for German Patent Application No. 10 2016 112 309.9, German Patent Office, dated May 9, 2017, 6 pp.
(Continued)

*Primary Examiner* — Paul M. West
*Assistant Examiner* — Mark A Shabman
(74) *Attorney, Agent, or Firm* — Christopher R. Powers; PatServe

(57) ABSTRACT

The present disclosure relates to an apparatus for determining and/or monitoring a process variable of a medium in a containment, including an oscillatable unit with a membrane, three rods secured to the membrane and extending perpendicularly to a base area of the membrane, a housing, wherein the rods extend into the housing a driving/receiving unit disposed at an end region of the rods and configured to excite the oscillatable unit and transduce mechanical oscillations into a received signal, and an electronics unit configured to produce an exciter signal from the received signal and to ascertain the process variable at least from the received signal. At least one of the rods is secured to the membrane at a site on the base area where the second (Continued)

derivative of the deflection of the membrane from a rest position as a function of the site on the base area is essentially zero.

15 Claims, 5 Drawing Sheets

(51) Int. Cl.
*G01N 11/16* (2006.01)
*G01P 5/02* (2006.01)
*G01N 11/00* (2006.01)

(52) U.S. Cl.
CPC .............. *G01N 11/16* (2013.01); *G01P 5/02* (2013.01); *G01N 2009/006* (2013.01); *G01N 2011/0073* (2013.01)

(56) References Cited

U.S. PATENT DOCUMENTS

| | | | | |
|---|---|---|---|---|
| 4,740,726 A | * | 4/1988 | Umezawa | G01F 23/2967 310/23 |
| 4,896,536 A | * | 1/1990 | Benz | G01F 23/2967 310/321 |
| 5,247,832 A | * | 9/1993 | Umezawa | G01F 23/2967 340/621 |
| 5,743,134 A | * | 4/1998 | Dreyer | G01F 23/2967 73/1.81 |
| 7,043,981 B2 | * | 5/2006 | Kuhny | B06B 1/0611 73/290 V |
| 2016/0069730 A1 | * | 3/2016 | Gruhler | G01F 23/2968 73/290 V |

FOREIGN PATENT DOCUMENTS

| | | |
|---|---|---|
| DE | 4203967 A1 | 8/1993 |
| DE | 102015104536 A1 | 9/2016 |
| EP | 0379855 A1 | 8/1990 |
| WO | 2004057283 A1 | 7/2004 |
| WO | 2005033635 A1 | 4/2005 |

OTHER PUBLICATIONS

International Search Report for Patent Application No. PCT/EP2017/065631, WIPO, dated Oct. 5, 2017, 13 pp.

* cited by examiner

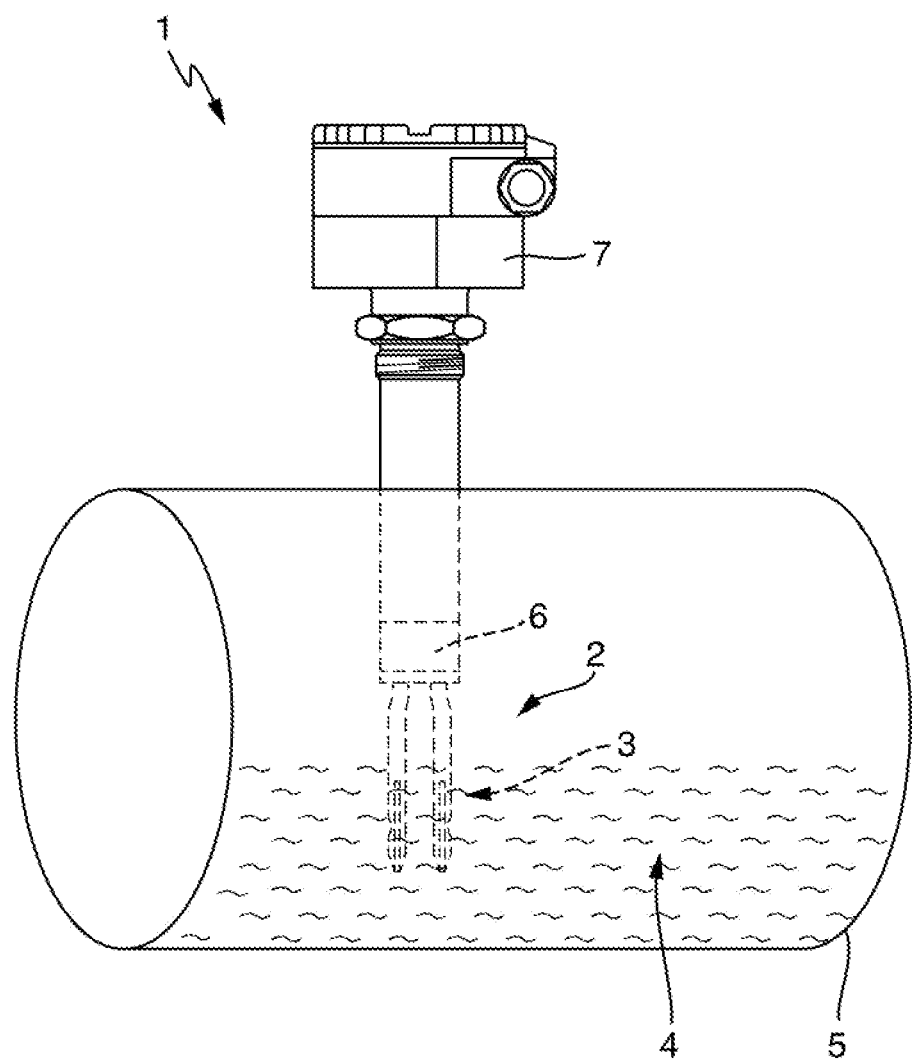
PRIOR ART  Fig. 1

APPARATUS FOR DETERMINING AND/OR MONITORING AT LEAST ONE PROCESS VARIABLE

CROSS-REFERENCE TO RELATED APPLICATIONS

The present application is related to and claims the priority benefit of German Patent Application No. 10 2016 112 309.9, filed on Jul. 5, 2016 and International Patent Application No. PCT/EP2017/065631, filed on Jun. 26, 2017 the entire contents of which are incorporated herein by reference.

TECHNICAL FIELD

The invention relates to an apparatus for determining and/or monitoring at least one process variable of a medium in a containment and comprises at least one driving/receiving unit, especially in the form of an electromechanical transducer unit. The process variable is, for example, the fill level or the flow velocity of the medium or even its density or viscosity. The medium is located, for example, in a container, a tank, or even in a pipeline.

BACKGROUND

In automation technology, the most varied of field devices are applied for determining and/or monitoring at least one process variable, especially a physical or chemical, process variable. Involved, for example, are fill-level measuring devices, flow measuring devices, pressure and temperature measuring devices, pH-redox potential measuring devices, conductivity measuring devices, etc., which register the corresponding process variables, fill level, flow, pressure, temperature, pH-value, and conductivity, etc. The associated measuring principles are known from a large number of publications.

A field device typically includes at least one sensor unit coming at least partially and at least at times in contact with the process, and an electronics unit, which serves, for example, for signal registration, evaluation and/or feeding. Referred to as field devices in the case of the present invention are, in principle, all measuring devices, which are applied near to the process and which deliver, or process, process relevant information, thus, also remote I/Os, radio adapters, and, generally, electronic components, which are arranged at the field level. A large number of such field devices are manufactured and sold by the Applicant.

In a number of corresponding field devices, electromechanical transducer units are used. An example of this are vibronic sensors, such as, for example, vibronic fill level or flow measuring devices. They are also used in ultrasonic, fill-level measuring devices or-flow measuring devices. To visit each type of field device having an electromechanical transducer unit and to explore underlying principles of the different types separately and in detail would be superfluous. Thus, for purposes of simplicity, where reference is taken to particular field devices, the following description is limited, by way of example, to fill-level measuring devices with an oscillatable unit.

The oscillatable unit of such fill-level measuring devices, also as referred to vibronic sensors, is, for example, an oscillatory fork, a single tine or a membrane. The oscillatable unit is excited during operation by means of a driving/receiving unit, usually in the form of an electromechanical transducer unit, to execute mechanical oscillations. The electromechanical transducer unit can be, for example, a piezoelectric, electromagnetic or even magnetostrictive driving/receiving unit. Corresponding field devices are manufactured by the Applicant in great variety and are sold, for example, under the marks, LIQUIPHANT and SOLIPHANT. The underpinning measuring principles are basically known. The driving/receiving unit excites the mechanically oscillatable unit by means of an electrical exciting signal to execute mechanical oscillations. Conversely, the driving/receiving unit can receive the mechanical oscillations of the mechanically oscillatable unit and convert them into an electrical, received signal. The driving/receiving unit can be either a separate driving unit and a separate receiving unit, or a combined driving/receiving unit.

For exciting the mechanically oscillatable unit, the most varied of methods, both analog as well as also digital, have been developed. In many cases, the driving/receiving unit is part of a fed back, electrical, oscillatory circuit, by means of which the exciting of the mechanically oscillatable unit to execute mechanical oscillations occurs. For example, for a resonant oscillation, the oscillatory circuit condition, according to which the amplification factor is $\geq 1$ as well as all phases arising in the oscillatory circuit must sum to a multiple of 360°, must be fulfilled. This has the result that a certain phase shift between the exciter signal and the received signal must be assured. For this, the most varied of solutions are known. In principle, the setting of the phase shift can be performed, for example, by application of a suitable filter, or even be controlled by means of a control loop to a predeterminable phase shift, the desired value. Known from DE102006034105A1, for example, is to use a tunable phase shifter. The additional integration of an amplifier with a tunable amplification factor for additional control of the oscillation amplitude was described, in contrast, in DE102007013557A1. DE102005015547A1 provides the application of an all-pass filter. The setting of the phase shift is, moreover, possible by means of a method involving frequency sweep, such as disclosed, for example, in DE102009026685A1, DE102009028022A1, and DE102010030982A1. The phase shift can, however, also be controlled by means of a phase control loop (phase-locked-loop, PLL) to a predeterminable value. Such an excitation method is subject matter of DE102010030982A'1.

Both the exciter signal as well as also the received signal are characterized by frequency, amplitude and/or phase. Changes in these variables are then usually taken into consideration for determining the particular process variable, such as, for example, a predetermined fill level of a medium in a container, or even the density and/or viscosity of a medium. In the case of a vibronic limit level switch for liquids, for example, of interest is whether the oscillatable unit is covered by the liquid or freely oscillating. These two states, the free state and the covered state, are, in such case, distinguished, for example, based on different resonance frequencies, thus, a frequency shift, or based on damping of the oscillation amplitude.

The density and/or viscosity can, in turn, only be ascertained with such a measuring device, when the oscillatable unit is covered by the medium. Known from DE10050299A1, DE102006033819A1 and DE102007043811A1 is to determine the viscosity of a medium based on the frequency-phase curve ($\phi$=g(f)). This procedure is based on the dependence of the damping of the oscillatable unit by the viscosity of the medium. In order to eliminate the influence of the density on the measuring, the viscosity is determined based on a frequency change caused by two different values for the phase, thus, by means of a relative measurement. For determining and/or monitoring the density of a medium, in contrast, according to DE10057974A1, the influence of at least one disturbing variable, for example, the viscosity, on the oscillation frequency of the mechanically oscillatable unit is ascertained and compensated. In DE102006033819A1, it is, furthermore, taught to set a predeterminable phase shift between the exciter signal and the received signal, in the case of which effects of changes of the viscosity of the medium on the mechanical oscillations of the mechanically oscillatable unit are negligible. At this phase shift, an empirical formula for determining the density can be created.

The driving/receiving unit is, as already mentioned, as a rule, embodied as an electromechanical transducer unit. Often, it includes at least one piezoelectric element in the most varied of embodiments. By using the piezoelectric effect, a high efficiency can be achieved. In such case, efficiency is with reference to the efficiency of changing electrical into mechanical energy. Corresponding piezoceramic materials based on LZT (lead zirconium titanate) are, normally, suitable for use at temperatures up to 300° C. There are piezoceramic materials, which keep their piezoelectric properties at temperatures above 300° C.; these have, however, the disadvantage that they are significantly less effective than the materials based on LZT. For use in vibronic sensors, these high temperature materials are, moreover, only conditionally suitable, due to the large differences in the coefficients of thermal expansion of metals and ceramic materials. Because of their function as force providers, the at least one piezoelectric element must be connected with a membrane (which is part of the oscillatable unit) by a force transmitting connection. Especially in the case of high temperatures, however, quite often, large mechanical stresses arise, which can lead to a breaking of the piezoelectric element and, associated therewith, a total failure of the sensor.

An alternative, which can be better suited for use at high temperatures, is provided by so-called electromagnetic driving/receiving units, such as, for example, described in the documents, WO 2007/113011 and WO 2007/114950 A1. The changing of electrical energy into mechanical energy occurs, in such case, via a magnetic field. A corresponding electromechanical transducer unit includes at least one coil and a permanent magnet. By means of the coil, an alternating magnetic field passing through the magnet is produced, and, via the magnet, a periodic force is transferred to the oscillatable unit. Usually, the transfer of this periodic force occurs similarly to the principle of the solenoid, which sits centrally on the membrane. In this way, the driving/receiving unit is applicable for a temperature range between −200° C. and 500° C. Often, there is, however, no force transmitting connection between the membrane and the driving/receiving unit, so that the efficiency of the field device is reduced compared with a piezoelectric driving/receiving unit.

Besides the applied driving/receiving unit, diverse electronic components, which usually are integrated into a field device as part an electronics unit, are limiting for the maximum process temperature, at which the particular field device can be applied. In order to decouple such temperature sensitive electronic components from a process, an established method provides integration of a so-called temperature spacing tube in the structure of a field device. For example, involved is a tube, which is part of the housing of the field device, and which is manufactured of a material distinguished by a high thermal insulation. In this regard, reference is made, for example, to EP2520892A1, in which is described the embodying of a section of the housing of a measuring device in such a manner that, in the presence of a temperature difference between an environment of the process connection and the electronics unit, a lower heat flow to the electronics unit occurs in parallel with a longitudinal axis of the housing.

In order to assure an as efficient as possible temperature decoupling of the driving/receiving unit from a process, known from the yet unpublished German patent application No. 102015104536.2 is an apparatus for determining and/or monitoring at least one process variable of a medium in a containment, in the case of which the driving/receiving unit is spatially separated from the process. This German patent application is incorporated by reference in the following.

SUMMARY

Starting from the above-described state of the art, an object of the present invention is to provide a field device having an electromechanical transducer unit, which compared to the state of the art is distinguished by an increased efficiency.

This object of the invention is achieved by an apparatus for determining and/or monitoring at least one process variable of a medium in a containment, comprising an oscillatable unit with at least one membrane, which can be caused to execute mechanical oscillations, at least three rods secured to the membrane and extending perpendicularly to a base area of the membrane, a housing, wherein the membrane forms at least a portion of a wall of the housing, and wherein the rods extend into the housing interior, at least one driving/receiving unit, which is arranged in the membrane far, end region of the rods, which driving/receiving unit is embodied to excite the oscillatable unit by means of an electrical exciting signal and by means of the rods to execute mechanical oscillations and to receive the mechanical oscillations of the oscillatable unit and to transduce them into an electrical, received signal, and an electronics unit, which is embodied to produce an exciter signal from the received signal, and to ascertain the at least one process variable at least from the received signal.

The housing as well as the rods serve for the spatial separation of the driving/receiving unit from the process. In this way, the apparatus of the invention is best for use in an expanded temperature range, especially for use at high temperatures. The direct, especially force transmitting, connection of the rods with the membrane assures, in spite of the spatial separation, a high efficiency of the force transfer from the driving/receiving unit two the oscillatable unit. In spite of this, the structural construction of an apparatus of the invention is comparatively simple.

The driving/receiving unit, especially an electromechanical transducer unit, can be both a separate driving unit and a separate receiving unit, or a combined driving/receiving unit. This can, for example, at least be secured to the two rods, wherein the securement especially involves a force transmitting connection. Alternatively, it can, however, also be arranged in such a manner within the housing that it does not contact the two rods.

Preferably, the driving/receiving unit is embodied to cause the rods to execute mechanical oscillations, wherein the rods are secured to the membrane in such a manner that oscillations of the membrane result from the oscillations of the rods. Thus, waves propagate along the rods with a wavelength λ predetermined by the driving/receiving unit. In this regard, the rods are pressed apart and drawn together frequency correctly by means of the driving/receiving unit. The rods behave correspondingly as a mechanical resonator. Since the rods are connected with the membrane, especially force transmittingly connected, thus, also the oscillatable unit is caused to execute mechanical oscillations. Conversely, the driving/receiving unit receives the waves, which, starting from the oscillatable unit, propagate along the two rods, and generates therefrom an electrical, received signal.

According to the invention, at least one of the rods is essentially secured to the membrane at a site on the base area of the membrane, where the second derivative of the deflection of the membrane from a rest position as a function of the site on the base area is essentially zero. Where on the base area of the membrane the second derivative of the deflection of the membrane from a rest position is essentially zero depends, among other things, on the oscillatory mode of the membrane.

At least one of the rods is, thus, essentially secured in the region of a point of inflection of the deflection from the rest position as a function of the location on the membrane. In such case, involved is the region, which at the time of a maximum oscillation amplitude of the membrane relative to a plane parallel with the base area of the membrane, thus, relative to the rest position, is the most curved. The rest position of the membrane is, in such case that position, in which no resulting force acts on the membrane, in which the membrane is, thus, not curved, but, instead, essentially planar.

Because of the positioning of the rods according to the invention, an especially efficient transfer of the oscillatory movements of the rods to the membrane is achieved. The apparatus has, thus, an especially high efficiency. In spite of this, the structural construction of an electromechanical transducer unit of the invention is comparatively simple. The required energy for operating the apparatus of the invention is, moreover, advantageously minimized in comparison with equivalent apparatuses.

In a preferred embodiment of the apparatus of the invention, the length L of the rods relative to the wavelength of the waves propagating along the rods amounts to $L=n\lambda/2+\lambda/4$, wherein n is a natural number. The length of the rods is, thus, fitted corresponding to a desired excitation frequency and as regards the required temperature decoupling.

In another preferred embodiment, the apparatus of the invention includes at least one securement element, by means of which at least two of the at least three rods are mechanically coupled with one another in the membrane far, end region. For this, the rods and the securement element are connected with one another, for example, by force transmitting connection. The rods are, thus, coupled with one another both by means of the membrane as well as also by means of the securement element. As in the case of an embodiment without securement element, the rods are pressed apart or drawn together frequency correctly by means of the driving/receiving unit in such a manner that a wave propagates along the rods and causes the oscillatable unit to execute mechanical oscillations. Independently of the number the rods, according to the invention, a single securement element can be applied for all rods. Alternatively, also individual portions of the total number of rods can be provided with different securement elements. The latter variant is advantageous especially for the case that not all of the rods have the same length.

In an embodiment of the apparatus of the invention, the frequency of the exciting signal and/or the length L of the rods is/are selected in such a manner that oscillations of the rods result in the propagation of standing waves along the rods. The propagation of standing waves along the rods is especially advantageous with reference to the efficiency of the apparatus of the invention.

In such case, it is especially advantageous that the length L of the rods relative to the wavelength of the waves propagating along the two rods amounts to $L=n\lambda/2$, wherein n is a natural number. The length of the rods is, thus, so adjusted corresponding to a desired excitation frequency and as regards the required temperature decoupling that standing waves can propagate.

Suited especially for an embodiment of the apparatus of the invention with a securement element is a driving/receiving unit comprising at least one piezoelectric element.

An especially preferred embodiment provides that the rods and/or the housing are manufactured of a material, which offers a good thermal insulation. This increases the degree of thermal insulation. The housing serves, thus, not only the function of protecting components contained therein, such as the rods. Rather, the housing serves also as a temperature spacing tube. The electronics unit can then be accommodated either in the process far region of the temperature spacing tube, or the housing includes a special region, within which the electronics unit is arranged. To that portion of the housing, which serves as a temperature spacing tube, especially, furthermore, the process connection is secured. The exact position of the process connection along the housing results, in such case, from the particular installation requirements.

Advantageously, the process variable is a fill level or the flow velocity of the medium in the containment, or by the density or the viscosity of the medium. For determining the process variables density and/or viscosity it is, furthermore, advantageous that the oscillatable unit be arranged in a defined position within the containment, in such a manner that it extends a determinable penetration depth into the medium.

On the one hand, the oscillatable unit can be a membrane oscillator. On the other hand, an embodiment provides that at least one oscillatory tine is secured to the membrane of the oscillatable unit. Then, the oscillatable unit is a single tine or, in the case of two oscillatory tines, for example, an oscillatory fork.

In a preferred embodiment, the driving/receiving unit comprises at least one piezoelectric element. Present is, thus, a piezoelectric transducer unit, such as, for example, a stack or bimorph drive. Alternatively, the driving/receiving unit can be an electromagnetic drive with at least one coil and a magnet. Furthermore, also magnetostrictive driving/receiving units are an option. Because of the spatial separation, the applied driving/receiving unit does not have to fulfill any special conditions as regards temperature sensitivity. It can rather be optimized relative to its efficiency as regards force transfer to the rods. In the case of a piezoelectric driving/receiving unit, this can be connected, for example, directly with the rods, wherein at least two of the rods, in turn, are preferably connected by means of a securement element. In the case of an electromagnetic driving/receiving unit, the rods, especially the magnets, which can be secured, for example, on the rods, should, however, not contact the coil. In this case, as a function of concrete embodiment, no securement element is necessary.

An embodiment of the apparatus of the invention provides that at least one of the rods is connected to the membrane essentially on a circular line extending around the midpoint of the base area of the membrane. This choice is especially advantageous for oscillations of the membrane in the fundamental oscillation mode, in the case of which the midpoint of the membrane experiences the greatest deflection. However, this embodiment is suitable also for higher oscillation modes, in the case of which the midpoint of the membrane experiences the greatest deflection. For higher oscillation modes, in such case, lines of nodes occur increasingly on the base area of the membrane.

An embodiment of the invention provides that the number of rods is an even number, wherein the rods are arranged symmetrically along the circular line around the midpoint of the membrane.

Alternatively, the number the rods is an odd number, wherein the rods are arranged at equal angles along the circular line around the midpoint of the membrane.

Depending on embodiment of the selected driving/receiving unit, it can be of advantage, when each of the rods has essentially the same separation from the driving/receiving unit.

In a preferred embodiment of the present invention, the oscillatable unit is an oscillatory fork having two tines, wherein the apparatus has four rods, and wherein two of the four rods secured to the membrane and the two oscillatory tines secured to the membrane are arranged oppositely lying and mirror symmetrically to one another with reference to a plane perpendicular to the longitudinal axis through the rods and/or oscillatory tines. In each case, an oscillatory tine and a rod extend, thus, essentially along the same imaginary line in parallel with their two longitudinal axes. Especially, these two rods and oscillatory tines are arranged in such a manner that they are located at the same distance from the midpoint of the base area of the membrane perpendicularly to the longitudinal axes of the rods and oscillatory tines. This symmetric arrangement in the case of a vibronic sensor with an oscillatory fork as oscillatable unit achieves an especially high efficiency.

The oscillatory tines, transducer rods and the membrane form a coupled oscillatory system, wherein the coupling is determined by the membrane. For the example of an oscillatable unit in the form of an oscillatory fork, for example, the two oscillatory tines and the membrane form a first mechanical resonator, the two rods lying opposite the oscillatory tines form with the membrane a second resonator and the two other rods and the membrane form a third resonator. The frequency of the exciting signal is preferably so selected that the first and second resonators oscillate in an antisymmetric, oscillatory mode with reference to the plane through the membrane perpendicular to the longitudinal axes of the transducer rods and/or oscillatory tines. In the oscillatory system formed, in principle, by three resonators, basically three resonance frequencies occur. This is described in more detail in connection with FIG. 5.

An alternative preferred embodiment of the present invention provides, likewise, that the oscillatable unit is an oscillatory fork having two tines. However, the apparatus has three rods, wherein the three rods are arranged in the corner points of an equal angled triangle arranged around the midpoint M of the membrane, in such a manner that the connecting line between two of the three transducer rods extends in parallel with a connecting line between the two oscillatory tines.

Arranging at least one of the transducer rods in a region of the membrane, which during the oscillatory movement experiences an especially large curvature, provides an especially high efficiency for transferring the oscillations from the transducer rods to the membrane and, in given cases, to the at least one oscillatory tine secured to the membrane. The efficiency grows, in such case, basically with the number of transducer rods used. However, a maximizing of the number of rods is limited by, among other things, the available space within the housing of the apparatus. It is to be noted here that the frequencies of the oscillatory movements are influenceable especially by adjusting the length and/or stiffness of the rods.

BRIEF DESCRIPTION OF THE DRAWINGS

The invention as well as advantageous embodiments thereof will now be described in greater detail based on the appended drawing, the figures of which show as follows:

FIG. 1 shows a schematic view of a vibronic sensor of the state of the art.

FIG. 4a shows curvature lines of a membrane for the apparatus of FIG. 2a;

DETAILED DESCRIPTION

Figure 2A:
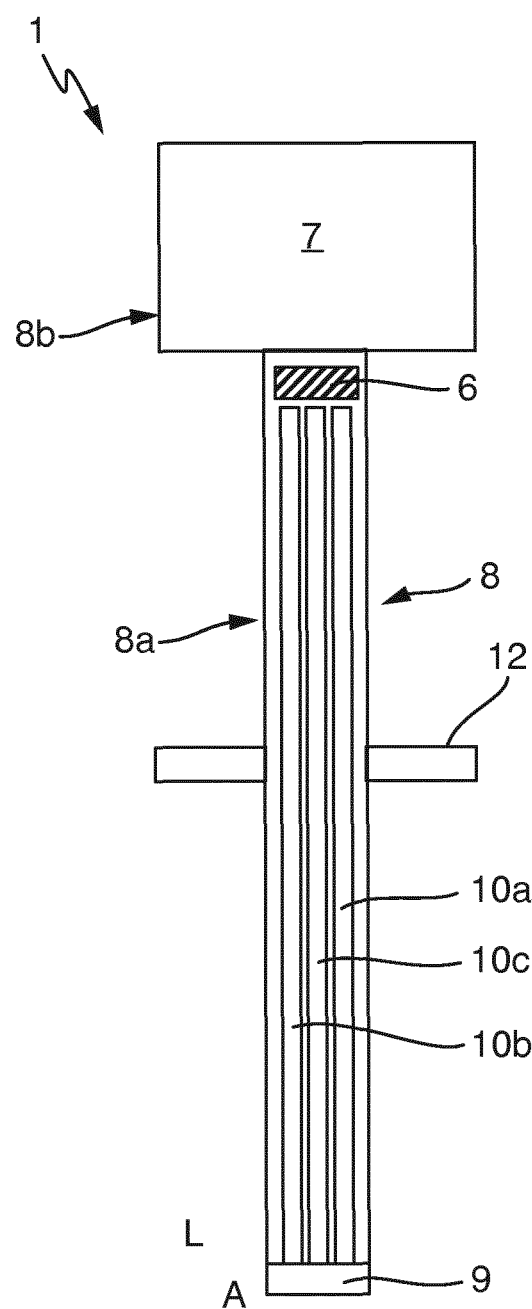
FIG. 2a shows an apparatus of the invention with an oscillatable unit including an oscillatory fork, without securement element and with four rods.

FIG. 1 shows a vibronic fill-level measuring device 1. A sensor unit 2 with a mechanically oscillatable unit 3 in the form of an oscillatory fork protrudes partially into a medium 4, which is located in a container 5. The oscillatable unit 3 is excited by means of the driving/receiving unit 6, as a rule, an electromechanical transducer unit, to execute mechanical oscillations. The exciting/receiving unit 6 can be, for example, a piezoelectric stack or bimorph drive, however, also an electromagnetic or even a magnetostrictive driving/receiving unit. It is understood, however, that also other embodiments of a vibronic fill-level measuring device are possible. Further provided is an electronics unit 7, by means of which signal registration, evaluation and/or feeding occurs.

FIG. 2a shows schematically a first embodiment of an apparatus 1 of the invention. In the lower wall of a housing 8 a membrane 9 is installed. At this location, the housing 8 is, thus, closed with the membrane 9. The housing 8 is cylindrical and the membrane 9 disc shaped with circularly round base area A. It is understood, however, that also other geometries are an option and fall within the scope of the present invention. Arranged secured to the membrane 9 perpendicularly to its base area A and extending inwardly into the interior of the housing 8 are four rods 10a, 10b, 10c, 10d (rod 10d is not visible in the illustrated view). In such case, the securement is especially via a force transmitting connection. The base area A of the membrane 9 lies in a plane perpendicular to the longitudinal direction of the four rods 10a-10d.

Arranged in the membrane 9 far, end region of the rods 10a-10d is a driving/receiving unit 6. This can, on the one hand, be secured at least to one of the rods 10a-10d. In the example shown here, the driving/receiving unit 6 is, however, arranged within the housing 8 in such a manner that it does not contact the rods 10a-10d. The driving/receiving unit 6 is an electromechanical transducer unit, especially a piezoelectric transducer unit with at least one piezoelectric element, or an electromagnetic transducer unit.

In the example shown in FIG. 2a, the housing is composed of two portions 8a, 8b. The first portion 8a surrounds at least the rods 10a-10d and the driving/receiving unit 6 and serves as a temperature spacing tube. The length of this temperature spacing tube is essentially matched to the length of the rods 10a-10d. In the second portion 8b, the electronics unit 7 is arranged. The two portions 8a, 8b are connected force transmittingly with one another and embodied in such a manner that signal conductive cable and the like can be led from the sensor unit 2 to the electronics unit 7. The connection between the two portions 8a, 8b can be, for example, a welded, adhesive soldered or brazed connection. Of course, the housing 8 can also comprise more portions or even be manufactured as one piece. In the middle region of the first portion 8a of the housing 8, further a process connection 12 is situated and connected fixedly with the housing 8. Here, the connection can likewise be, for example, a welded, adhesive soldered or brazed connection. The exact position of the process connection 12 is determined, in each case, based on the individual installed situation.

In the ongoing operation, the driving/receiving unit 6 is supplied with an exciter signal in the form of an alternating electrical current or alternating voltage signal in such a manner that the driving/receiving unit 6 the rods 10a-10d are moved in the membrane 9 far, end region frequency correctly apart and/or together, in such a manner that the rods 10a-10d are caused to oscillate. As a result, waves propagate along the rods 10a-10d, which, due to a lever effect, lead to an oscillatory movement of the oscillatable unit 3, thus, in this case, the membrane 9. In such case, the length of the rods 10a-10d and the frequency of the exciting signal are matched to one another taking into consideration the requirements relative to the temperature decoupling. Depending on choice of the frequency of the exciting signal and the length of the rods 10a-10d, preferably standing waves arise, which leads to an especially high efficiency as regards the force transfer to the membrane 9.

On the other hand, the driving/receiving unit receives the amplitude of the waves, especially standing waves, which propagate starting from the oscillatable unit 3 along the rods 10a-10d, and converts these into an electrical, received signal. The rods 10a-10d form, in such case, together with the membrane 9, a mechanical resonator.

Figure 2B:
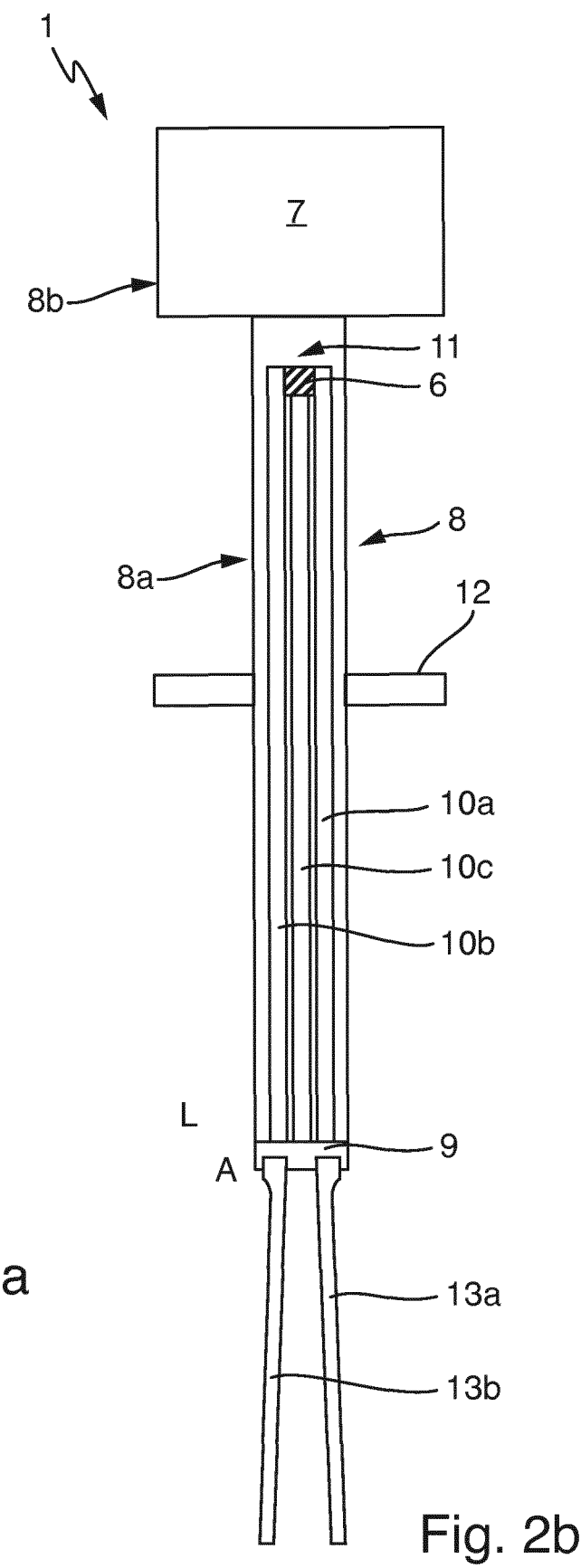
FIG. 2b shows an apparatus of the invention with an oscillatable unit including an oscillatory fork with securement element and with three rods.

Optionally secured to the housing 8 far side of the membrane 9, such as shown in FIG. 2b based on the apparatus of the invention with three rods 10a-10c, of course, also for the case of four rods 10-10d, can be two oscillatory tines 13a, 13b, which are connected force transmittingly with the membrane 9. Then the oscillatable unit 3 is an oscillatory fork. It is understood, however, that the oscillatable unit 3 could also be, for example, a single tine.

An alternative embodiment of an apparatus 1 of the invention very similar to that of FIG. 2a is shown in FIG. 2b. In contrast to the embodiment of FIG. 2a, the apparatus 1 of FIG. 2b has, however, only three rods 10a-10c. In addition to the components described in connection with FIG. 2a, furthermore in FIG. 2b, a securement element 11 is present in the membrane 9 far, end region of the rods 10a-10c. Securement element 11 can be, for example, disc shaped and have a round cross sectional area, or have generally the same base area A' as that of the membrane 9. Also more than one securement element 11 can be provided, wherein, in each case, one securement element 11 connects at least two of the rods 10a-10c. The driving/receiving unit 6 is arranged in the direct vicinity of the securement element 11 on the side of the securement element 11 facing the membrane 9. It is to be noted, however, that also other arrangements are possible. In this example, the driving/receiving unit 6 is secured especially at least to the rods 10a-10c, especially force transmitting secured. The rods 10a-10c are, thus, coupled with one another in one of their end regions via the membrane 9 and coupled in the second end region via the securement element 11. In the case of such an embodiment, the driving/receiving unit 6 preferably includes at least one piezoelectric element.

Figure 3A:
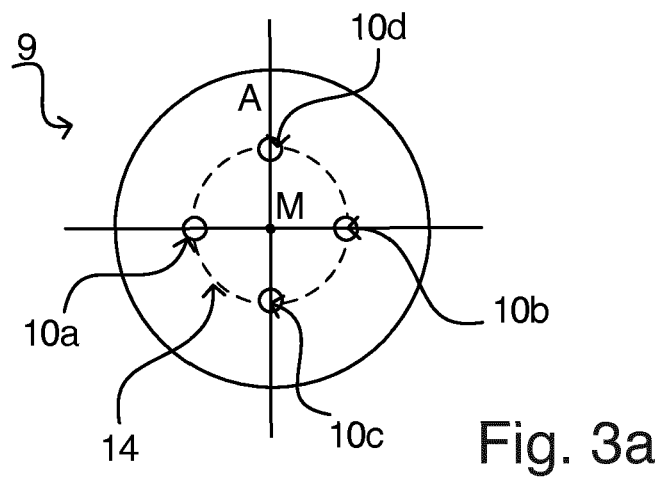
FIG. 3a shows a schematic arrangement of rods on a base area of a membrane for an apparatus of the invention with an oscillatable unit including the membrane and four rods.
Figure 3B:
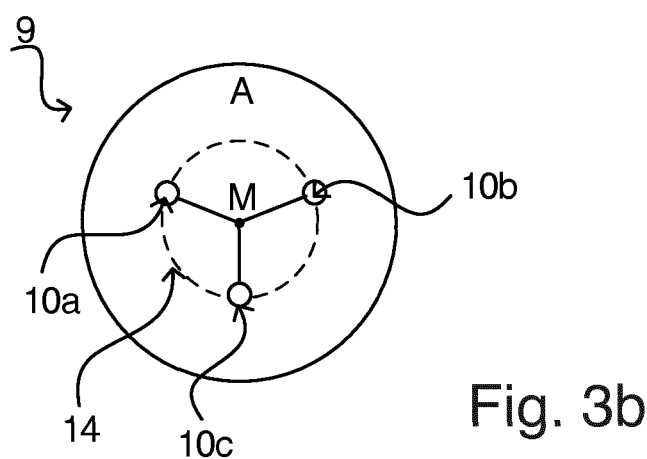
FIG. 3b shows a schematic arrangement of rods on a base area of a membrane for an apparatus of the invention with an oscillatable unit including the membrane and three rods.

According to the invention, at least one of the rods 10a-10d is essentially secured on the membrane 9 at a site on the base area of the membrane 9, where the second derivative of the deflection of the membrane 9 from a rest position as a function of the site on the base area A is essentially zero. In the case of a circularly round membrane 9 with the base area A, which executes oscillations in the fundamental oscillation mode, this region is essentially defined by a circular line 14 extending around the midpoint M of the membrane, as shown in FIGS. 3a and 3b. In the case of higher oscillation modes, lines of nodes form increasingly on the membrane 9, so that, as a function of oscillatory mode, also a number of regions can exist on the base area A of the membrane 9, where the second derivative of the deflection is essentially zero.

Preferred positionings of the rods 10a-10d on the base area of a membrane 9 with circularly round base area A for different numbers of rods 10a-10d are shown in FIG. 3. In the example of an embodiment of FIG. 3, four rods 10a-10d, each indicated by a circle, are arranged in the region of the circular line 14, in such a manner that, in each case, two rods 10a and 10b, and 10c and 10d, lie opposite one another. For the case of three rods 10a-10c, as shown in FIG. 3b, the rods are arranged, in contrast, preferably at equal angles along the circumference of the circular line.

Figure 4A:
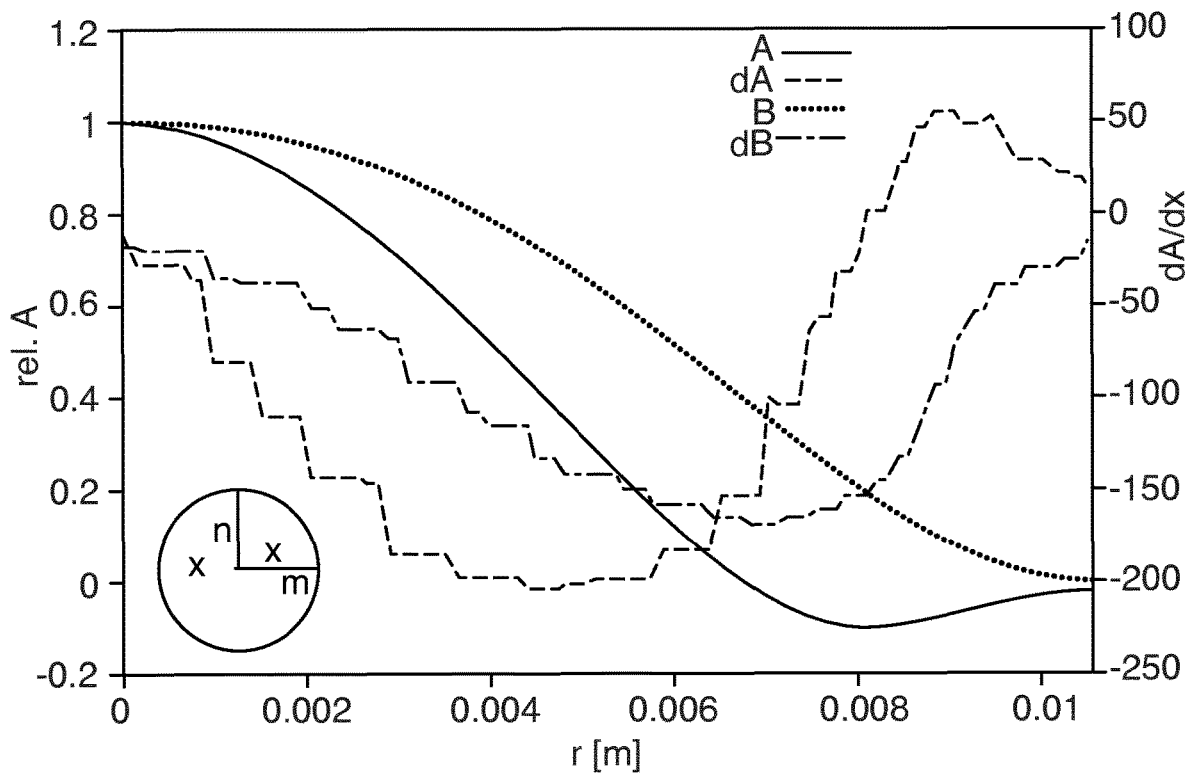

In the case of an oscillatable unit in the form of a membrane 9, the apparatus 1 of the invention is a mechanical resonator. In the case, in contrast, in which at least one oscillatory tine 13a, 13b is associated with the oscillatable unit 3, so that especially a single tine or an oscillatory fork is present, is a coupled resonator system is formed, for which a number of oscillation modes and resonance frequencies occur. For the example of an apparatus 1 of the invention with four rods 10a-10d, without securement element 11 and an oscillatable unit 3 in the form of an oscillatory fork, for example, the two oscillatory tines 13a, 13b of the oscillatable unit 3 form with the membrane 9 a first mechanical resonator, while the two pairs of rods 10a, 10b, and 10c, 10d, form with the membrane 9 second and third mechanical resonators, respectively. All three resonators are mechanically coupled with one another via the membrane 9, wherein the coupling is adjustable via the embodiment of the membrane 9. For example, the coupling can be influenced via the wall thickness or the material of the membrane 9, however, also by the particular connections with the oscillatory tines 13a, 13b or rods 10a-10d. The occurrence of these oscillation modes is explained below based on the FIGS. 4 and 5.

The changed oscillatory behavior due to the presence of at least one oscillatory tine 13a, 13b can be explained the easiest, for example, based on an oscillatable unit 3 in the form of an oscillatory fork. This is apparent, for example, from the curvature lines of the membrane 9 from its midpoint M to its edge along the two lines m and n shown in FIG. 4a, wherein the line m extends in parallel with an imaginary connecting line on the base area A of the membrane 9 through the two oscillatory tines 13a and 13b, and line n is perpendicular to line m. The two oscillatory tines 13a, 13b are indicated here by the two xs. The curvature lines along the lines n and m are, in contrast to the embodiment of FIG. 3, no longer symmetrical. This happens especially because the stiffnesses of the membrane 9 along the two lines m and n differ from one another. As a result, the locations on the base area A of the membrane 9, where the second derivative of the deflection of the membrane 9 from its rest position is essentially equal to zero, are no longer given by a circular line 14, but, instead, by an ellipse 23.

For an as efficient as possible energy transfer from the rods 10a-10d to the membrane 9, it is correspondingly advantageous to arrange the rods 10a-10d along the ellipse 23 extending around the midpoint M of the base area A of the membrane 9. Then all rods 10a-10d would be arranged in the region of maximum curvature of the membrane 9, thus, where the rods 10a-10d each experience in the region secured to the membrane 9 a maximum deflection. Furthermore, it is advantageous that the separation of each of the rods 10a-10d from an axis extending perpendicular to the base area A of the membrane through the midpoint M of the base area A of the membrane 9 be essentially equal, in order that the rods 10a-10d are displaced uniformly for oscillation. If one desires the best compromise between these two requirements, for example, the preferred arrangements shown in FIGS. 4b and 4c for the case of a apparatuses with three and four rods 10a-10d can be recommended.

Figure 4B:
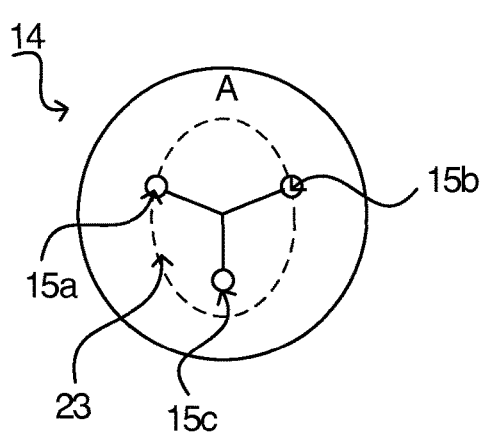
FIG. 4b shows an arrangement of rods on the base area of the membrane in an embodiment including four rods.

In the case of three rods 10a-10c, these are arranged in the corner points of an equal angled triangle extending around the midpoint M of the membrane 9, as shown in FIG. 4b. The connecting line between two 10a, 10b of the three rods 10a-10c extends in parallel with a connecting line between the two tines 13a, 13b. For the embodiment of FIG. 4b, the two rods 10a, 10b are, furthermore, arranged at a site on the base area A of the membrane 9, which during the oscillatory movement experiences the greatest curvature, where the second derivative of the deflection of the membrane 9 from the rest position is, thus, essentially zero. Alternatively, it is likewise an option that only one of the three rods 10a-10c is arranged at a site on the base area A of the membrane 9, where the second derivative of the deflection of the membrane 9 is essentially zero. Then, preferably the connecting line between the two other of the three rods 10a-10c extends in parallel with a connecting line between the two tines 13a, 13b.

Figure 4C:
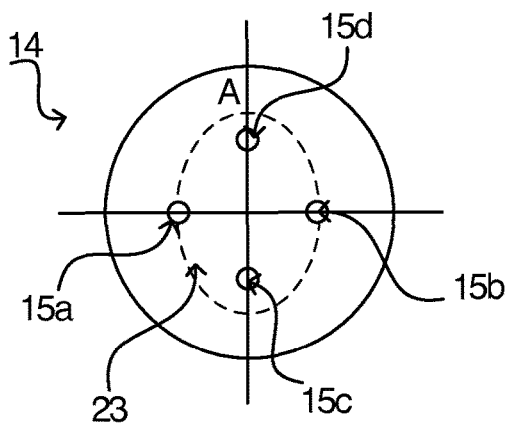
FIG. 4c shows an arrangement of rods on the base area of the membrane in an embodiment including three rods.

As evident from FIG. 4c, in the case of four rods 10a-10d, the rods 10a-10d are, in contrast, similarly to the case of an oscillatable unit in the form of a membrane 9 as shown in FIG. 3, preferably arranged along a circular line around the midpoint M of the base area A of the membrane 9, so that, in each case, two of the four rods 10a-10d lie opposite one another across the midpoint M of the base area A of the membrane 9. This has the result that, in contrast to the embodiment of FIG. 3, in this example, only two of the four rods 10a-10d are arranged at a site on the base area A of the membrane 9, where the second derivative of the deflection is essentially zero, since these locations are described by the ellipse 23.

Preferably, the two oscillatory tines 13a, 13b and the two rods 10a, 10b of the four rods 10a-10d are secured on the membrane 9 in such a manner that, in each case, a pair formed of one rod and one oscillatory tine, i.e. 10a and 13a in one case, and 10b and 13b any other case, extend along a longitudinal axis common to the pair and extending perpendicularly to the base area A through the membrane 9. In such case, the two longitudinal axes intersect a plane parallel to the membrane 9 at the same distance from the midpoint of the area A. This symmetric arrangement is especially advantageous relative to the efficiency of the apparatus.

The coupled resonator system occurring in the case of an oscillatable unit 3 in the form of an oscillatory fork (and even in the case of a single tine) functions similarly to the system described in the yet unpublished German patent application No. 102015104536.2. For the sake of convenience, such a coupled resonator system is explained below based on FIG. 5 for the case of an electromechanical transducer unit with four rods 10a-10d, as shown in FIG. 4c. For the case of an uneven number of rods, especially in the case of three rods 10a-10c, similar considerations hold. It is noted, however, that in comparison with an arrangement with an even number of rods 10a-10d, especially due to the respective symmetries of the arrangements, relatively more complex oscillation modes can occur.

Figure 5:
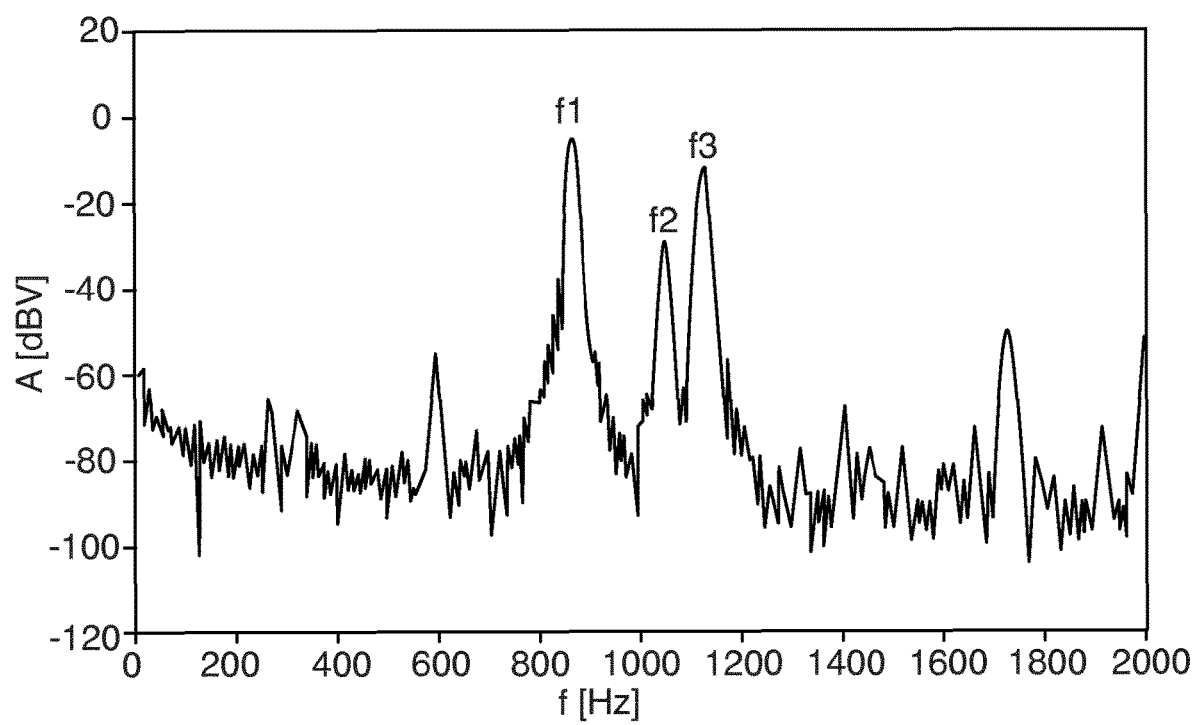
FIG. 5 shows a frequency spectrum of a vibronic sensor with an oscillatable unit including an oscillatory fork and four rods.

In a coupled resonator system having four rods 10a-10d and an oscillatable unit 3 in the form of an oscillatory fork, three resonance frequencies occur, of which one belongs to an antisymmetric oscillation mode and two to symmetric oscillation modes, such as evident from the frequency spectrum in FIG. 5, where the medium was air. The antisymmetric, oscillatory mode f1 lies in the case of this example of a frequency spectrum at about 864 Hz, while the two symmetric oscillation modes f2 and f3 lie at 1050 Hz and at 1135 Hz. In the case of the antisymmetric, oscillatory mode with the frequency f1, the rods 10a-10d move in the membrane 9 far region toward one another, when the two oscillatory tines 13a, 13b move in the membrane 9 far region away from one another. This oscillatory mode corresponds to the natural oscillatory movement of the oscillatory fork 3, for example, an oscillatory fork 3 applied in an LIQUIPHANT or SOLIPHANT instrument. The symmetric oscillation modes, in contrast, move the two oscillatory tines 13a, 13b in the membrane 9 far region likewise toward one another, when the rods 10a-10d in the membrane 9 far region move toward one another. For the symmetric oscillation modes with the resonance frequencies f2 and f3, in each case, the oscillation amplitude of one of the two rod pairs 10a and 10b, and 10c and 10d, is slightly greater than that of the other rod pair. In case of resonance frequencies of the individual oscillation modes f1-f3 lying near enough relative to one another, this is, however, insignificant and the rods 10a-10d and the oscillatory tines 13a, 13b oscillate essentially with equal amplitude.

In summary, the apparatus of the invention is best suited for use in an expanded temperature range, especially for used at high temperatures. The maximum allowable process temperature is, in such case, essentially only determined by the material properties of the oscillatable unit 3 and by the length and the material of the housing 8, especially the temperature spacing tube. The length of the rods 10a-10d and the housing 8 can, in such case, be lengthened in multiple half wavelengths of the standing waves and matched, in each case, to the existing temperature requirements. In such case, no special temperature requirements for the driving/receiving unit 6 must be met.

The invention claimed is:

1. An apparatus for determining and/or monitoring a process variable of a medium in a containment, the apparatus comprising:
   an oscillatable unit with a membrane having a base area, which can be caused to execute mechanical oscillations;
   at least three rods attached to the membrane and extending perpendicular to the base area of the membrane;
   a housing, wherein the membrane forms at least a portion of a wall of the housing, and wherein the rods extend into the housing;
   a driving/receiving unit disposed opposite the membrane in an end region of the at least three rods
   and configured to excite the oscillatable unit using an electrical exciting signal via the at least three rods to execute mechanical oscillations, to receive the mechanical oscillations of the oscillatable unit, and to transduce the mechanical oscillations into an electrical received signal; and
   an electronics unit configured to generate an exciter signal from the received signal and to ascertain the process variable at least from the received signal,
   wherein at least one of the at least three rods is attached to the membrane at a site on the base area where a second derivative of a deflection of the membrane from a rest position as a function of the site on the base area is essentially zero.

2. The apparatus of claim 1, wherein a length of any of the at least three rods relative to a wavelength of waves propagating along each rod is:

$$L=n\cdot\lambda/2+\lambda/4,$$

wherein L is the length and n is a natural number.

3. The apparatus of claim 2, further comprising at least one securement element by which at least two of the at least three rods are mechanically coupled to one another in the end region opposite the membrane.

4. The apparatus of claim 3, wherein a frequency of the exciting signal and/or the length is/are selected such that oscillations of the at least three rods result in the propagation of standing waves along the rods.

5. The apparatus of claim 3, wherein the length relative to a wavelength of waves propagating along the two rods is:

$$L=n\cdot\lambda/2,$$

wherein n is a natural number.

6. The apparatus of claim 1, wherein the at least three rods and/or the housing are manufactured of a thermally insulating material.

7. The apparatus of claim 1, wherein the process variable is a predetermined fill level, a flow velocity, a density or a viscosity of the medium.

8. The apparatus of claim 1, wherein at least one oscillatory tine is attached to the membrane of the oscillatable unit.

9. The apparatus of claim 1, wherein the driving/receiving unit includes at least one piezoelectric element.

10. The apparatus of claim 1, wherein the driving/receiving unit includes an electromagnetic drive with at least one coil and a magnet.

11. The apparatus of claim 1, wherein at least one of the at least three rods is connected to the membrane on a circular line extending around a midpoint of the base area of the membrane.

12. The apparatus of claim 1, wherein the number the at least three rods is an even number, and wherein the even number of rods are arranged symmetrically along a circular line around a midpoint of the membrane.

13. The apparatus of claim 1, wherein the number the at least three rods is an odd number, and wherein the odd number of rods are arranged at equal angles along a circular line around a midpoint of the membrane.

14. The apparatus of claim 1, wherein the oscillatable unit is an oscillatory fork having two oscillatory tines attached to the membrane, wherein the apparatus has four rods, and wherein two of the four rods attached to the membrane and the two oscillatory tines are arranged opposite one another mirror symmetrically with reference to a plane perpendicular to a longitudinal axis through the rods and/or oscillatory tines.

15. The apparatus of claim 1, wherein the oscillatable unit is an oscillatory fork having two oscillatory tines, wherein the apparatus has three rods, and wherein the three rods are arranged at corner points of an equilateral triangle extending around a midpoint of the membrane such that a connecting line between two of the three rods extends in parallel with a connecting line between the two oscillatory tines.

* * * * *